United States Patent [19]

Haley

[11] Patent Number: 5,635,489

[45] Date of Patent: Jun. 3, 1997

[54] METHODS OF PREVENTION OF ORAL MUCOSITIS WITH TRANSFORMING GROWTH FACTOR β

[75] Inventor: John D. Haley, Great Neck, N.Y.

[73] Assignee: Oncogene Science, Inc., Uniondale, N.Y.

[21] Appl. No.: 395,909

[22] Filed: Feb. 28, 1995

Related U.S. Application Data

[63] Continuation of Ser. No. 992,479, Dec. 15, 1992, abandoned, which is a continuation-in-part of Ser. No. 948,005, Sep. 21, 1992, abandoned.

[51] Int. Cl.$^6$ .............................. A61K 38/00; C07K 2/00; C07K 4/00
[52] U.S. Cl. .............................. 514/21; 514/12; 424/85.1
[58] Field of Search .................... 514/12, 21; 424/85.1

[56] References Cited

U.S. PATENT DOCUMENTS

| | | | |
|---|---|---|---|
| 4,863,902 | 9/1989 | Amagase | 514/12 |
| 4,929,442 | 5/1990 | Powell | 424/85.2 |
| 5,102,870 | 4/1992 | Florine et al. | 514/12 |
| 5,104,977 | 4/1992 | Sporn | 530/399 |
| 5,108,989 | 4/1992 | Amento | 514/12 |
| 5,147,854 | 9/1992 | Newman | 514/12 |

FOREIGN PATENT DOCUMENTS

| | | |
|---|---|---|
| 190018 | 8/1986 | European Pat. Off. |
| 290018 | 11/1988 | European Pat. Off. |
| WO89/04664 | 6/1989 | WIPO |
| WO89/06139 | 7/1989 | WIPO |
| WO92/14480 | 9/1992 | WIPO |
| WO92/18153 | 10/1992 | WIPO |

OTHER PUBLICATIONS

Brown et al. "Enhancement of Epidermal Regeneration by Biosynthetic Epidermal Growth Factor," Journal of Experimental Medicine, vol. 163, pp. 1319–1324, (1986), (Ex. 11).

Epstein, "The Painful Mouth," Infectious Syndromes of the Head and Neck, vol. 2, pp. 183–202. (1988), (Ex. 12).

Gabrilove et al., "Effect of Granulocyte Colony–Stimulating Factor on Neutropenia and Associated Morbidity Due to Chemotherapy for Transitional–Cell Carcinoma of the Urothelium," New England Journal of Medicine, vol. 318, pp. 1414–1422 (1988), (Ex. 13).

Konturek et al., "Gastric Cytoprotection by Epidermal Growth Factor," Gastroenterology, vol. 81, pp. 438–443. (1981), (Ex. 14).

Lawrence et al., "Reversal of an Admiamycin Induced Healing Impairment with Chemottractants and Growth Factors," Ann. Surg., vol. 203, pp. 142–147, (1984), (Ex. 15).

Niall et al., "The Effect of Epidermal Growth Factor on Wound Healing in Mice," Journal of Surgical Research, vol. 33, pp. 164–169. (1982), (Ex. 16).

Peterson et al., "Oral Complications of Cancer Chemotherapy: Present Status and Future Studies," Cancer Treatment Reports, vol. 66, pp. 1251–1256. (1982), (Ex. 17).

Robinson et al., "Epidermal Growth Factor (hEGF) Has No Effect on Murine Intestine Epithelial Damage and Regeneration After Melphalan," Br. J. Cancer, vol. 52, pp. 733–737, (1985), (Ex. 18).

Sonis et al., "An Animal Model for Mucositis Induced by Cancer Chemotherapy," Oral Surg. Oral Med. Oral Pathol., vol. 69, pp. 437–443, (1990), (Ex. 19).

Sonis et al., "Effect of Epidermal Growth Factor on Ulcerative Mucositis in Hamsters That Receive Cancer Chemotherapy," Oral Surg. Oral Med. Oral Pathol., vol. 74, pp. 749–755, (1992), (Ex. 20).

Southgate et al., "Primary Culture of Human Oral Epithelial Cells," Laboratory Investigation, vol. 56, pp. 211–223. (1987), (Ex. 21).

Steidler et al., "Histomorphological Effects of Epidermal Growth Factor on Skin and Oral Mucosa in Neonatal Mice," Archives or Oral Biology, vol. 25, pp. 37–43, (1980) (Ex. 22).

Primary Examiner—Jill Warden
Assistant Examiner—P. Lynn Touzeau
Attorney, Agent, or Firm—John P. White

[57] ABSTRACT

The present invention provides methods of preventing oral mucositis in a subject susceptible to mucositis which comprises administering to the subject a prophylactically effective amount of TGF-β3. Typically, administration is topical and initiated prior to anti-neoplastic therapy such as radiation treatment or chemotherapy. The invention is particularly suited for pediatric patients.

9 Claims, 11 Drawing Sheets

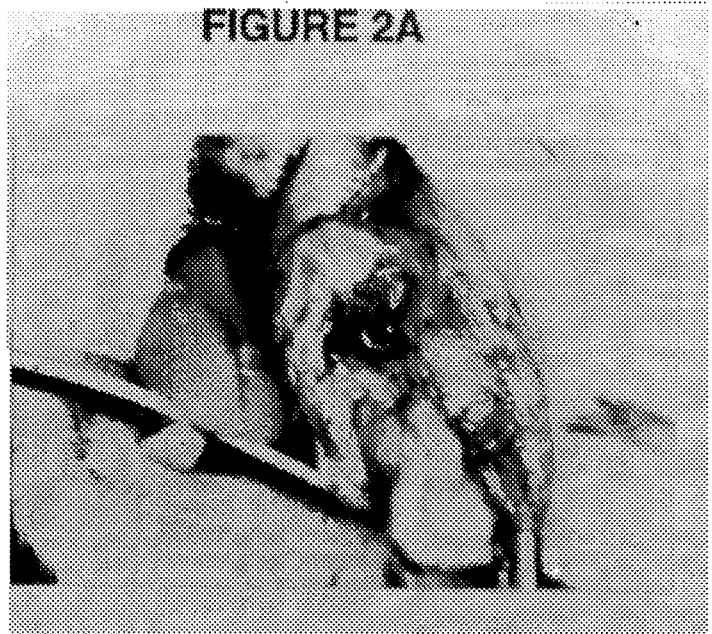
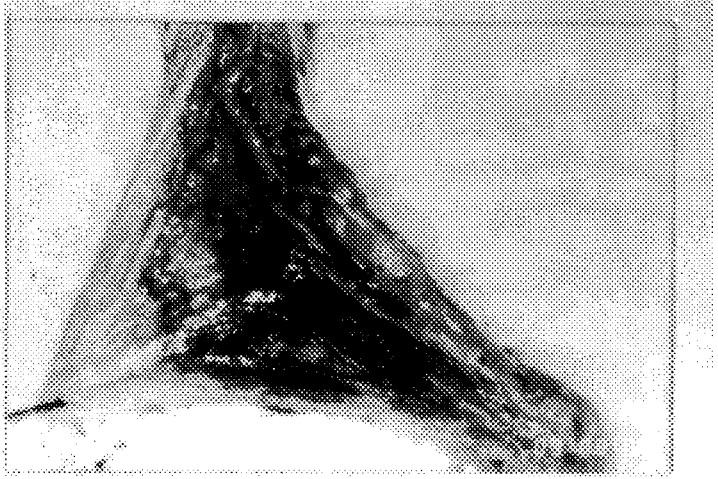
FIGURE 2A
Group 1
Group 2
Group 3

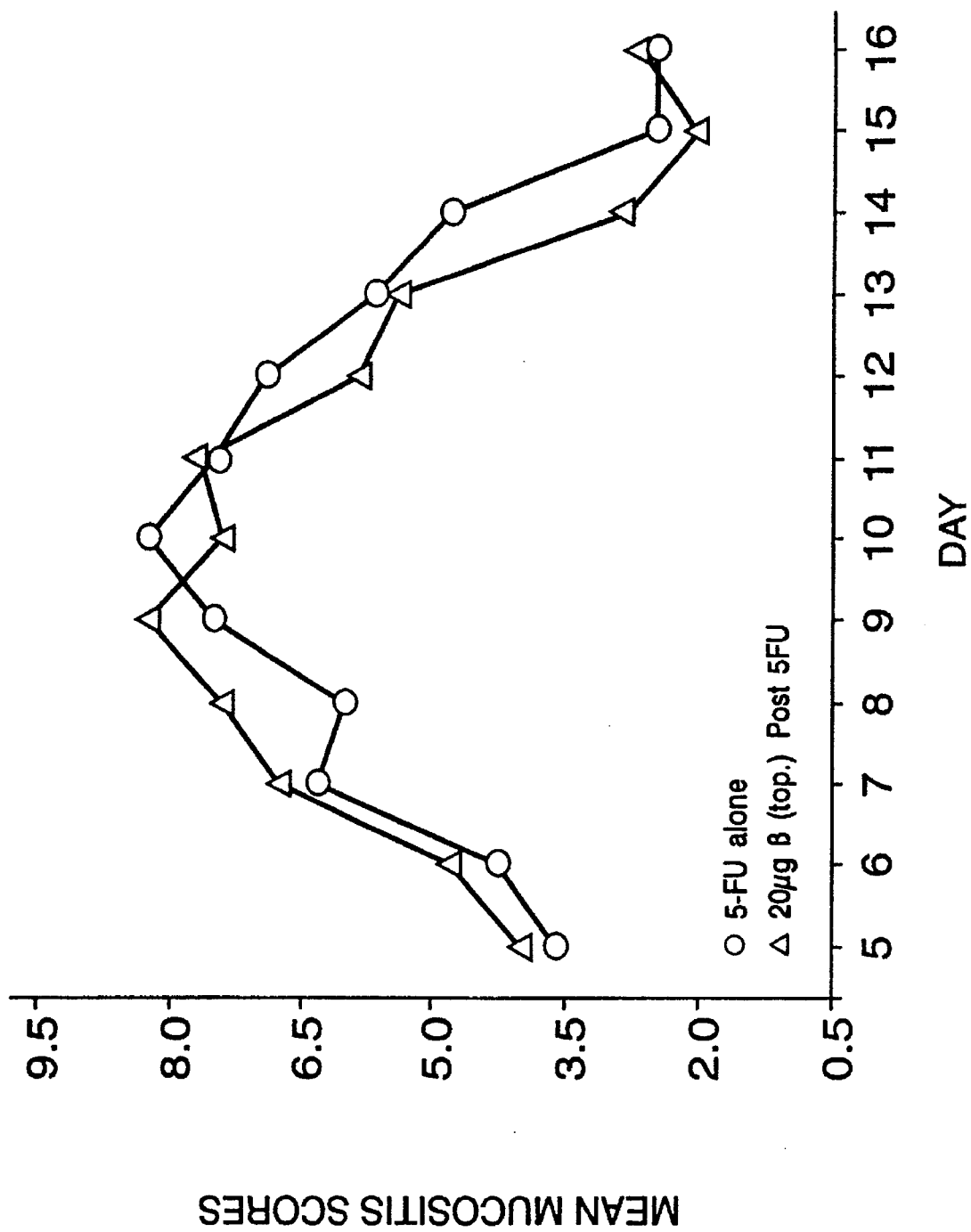

METHODS OF PREVENTION OF ORAL MUCOSITIS WITH TRANSFORMING GROWTH FACTOR β

This application is a continuation of U.S. Ser. No. 07/992,479 now abandoned, which is a continuation-in-part of U.S. Ser. No. 948,005, filed Sep. 21, 1992, now abandoned, the contents of which are incorporated by reference into the present application.

Throughout this application, various publications are referenced by author and date. Full citations for these publications may be found listed alphabetically at the end of the specification immediately preceding the claims. The disclosures of these publications in their entireties are hereby incorporated by reference into this application in order to more fully describe the state of the art as known to those skilled therein as of the date of the invention described and claimed herein.

BACKGROUND OF THE INVENTION

Currently, 800,000 patients receive chemotherapy in the United States each year. Myelosuppression and oral toxicity are common in conventional chemotherapy and are exacerbated by high dose and/or schedule intensification. As chemotherapeutic dosage has been identified as a major predictor of treatment outcome in a variety of cancer treatment programs, overcoming dose limiting toxicity has become a major goal for oncologists. Thus, to allow intensification of chemotherapy, it will be essential to prevent these unwanted side effects.

Studies have shown that oral toxicity is a major problem in the clinic (Guggenheimer et al., 1977; Lockhart et al., 1981; Sonis et al., 1988; and Sonis & Clark, 1991). This toxicity is very common and is often dose or schedule limiting in both standard and high dose chemotherapy. As improvements are made in management of hematopoietic toxicity, oral toxicity is more frequently dose and schedule limiting. For example, many of colon cancer patients receiving 5-fluorouracil (5-FU) suffer from oral mucositis. It has been estimated that 40% of chemotherapy patients develop oral complications (Sonis et al., 1978). For example, 67% of leukemia/lymphoma patients, 75% of patients receiving bone marrow transplants following therapy, and approximately 20% of breast cancer patients, suffer from oral mucositis.

Chemotherapy agents which cause oral mucositis include commonly prescribed agents. Single-agent or combination therapies which result in dose or schedule limiting oral and gastrointestinal (GI) toxicity include, but are not limited to, 5-FU, methotrexate, doxorubicin, Melphalan, and AFM regimen, the CEA regimen and the CAF regimen (Sonis et al., 1990).

Oral mucositis following chemotherapy is a consequence of the high proliferative rate of the normal epithelial cells lining the oral cavity. Chemotherapy-induced mucositis in the oral cavity is largely derived from injury to the basal epithelial cell layer. The epithelial lining of the mouth is generally five cells thick, with the self-renewing stem cell layer located at the base, which itself overlays a fibrous connective tissue matrix. In contrast to skin, most of the epithelium which lines the oral cavity are not highly keratinized, and therefore are able to absorb and elicit a biological response to exogenously added peptide growth factors. The epithelium at the base of the mouth divides most rapidly and is most sensitive to chemotherapy.

The extent of oral mucositis appears dependent on the cycling status of the epithelial cell layer. For example, 90% of pediatric chemotherapy patients (ages 1–20) develop oral mucositis, as compared with 18% of patients over the age of sixty (Sonis et al., 1979). Further, in animal models of oral mucositis, increasing proliferation of the oral epithelium by prior administration of growth factor (e.g. EGF, TGF-α) markedly increases the severity of oral mucositis.

Mucositis results from epithelial thinning and ulceration resulting in severe pain, weight loss from failure to eat or drink (often requiring parenteral feeding), infection (bacterial, fungal and viral), fever, nausea and diarrhea. Symptoms peak 7 to 10 days following therapy, and gradually recede over the following two weeks. The major complications which accompany mucositis include severe pain, pronounced reduction in food and fluid intake and potentially life-threatening infection due to sepsis. Therefore, method& of preventing oral toxicity enable escalated schedules and doses of a chemotherapy regimen, resulting in improved patient long term survival for many human cancers, notably leukemia, lymphoma, testicular, neuroblastoma and breast cancer.

The ability of growth factors to accelerate healing is well known. Recently, U.S. Pat. No. 5,102,870, issued Apr. 7, 1992 from U.S. Ser. No. 339,463, filed Apr. 14, 1989, described the use of growth factors to aid in the healing of oral mucositis. Such factors are used to accelerate healing of the oral mucositis, administered after exposure to the radiation or chemotherapy. This and related approaches aid in healing subsequent to the exposure, they do not address the high proliferative rate of normal epithelial cells that makes them vulnerable to the antineoplastic agents vide supra. As described above administration of growth factors prior to chemotherapy leads to more severe oral mucositis. Therefore methods of slowing the high proliferative rate of oral epithelial cells could have great potential.

SUMMARY OF THE INVENTION

The present invention provides a method of preventing oral mucositis in a subject susceptible to mucositis which comprises administering to the subject a prophylactically effective amount of a Transforming Growth Factor Beta. Typically, administration is topical and initiated prior to anti-neoplastic therapy such as radiation treatment or chemotherapy. The invention is particularly suited for pediatric patients.

BRIEF DESCRIPTION OF THE FIGURES

FIG. 9: Mean mucositis scores for Group 1 (open circles): 5-FU alone. Group 5: (open triangles) 5-FU and additional 20 µg TGFβ3 topically administered post 5-FU, twice daily on days 5, 6 and 7.

DETAILED DESCRIPTION OF THE INVENTION

Figure 1A:
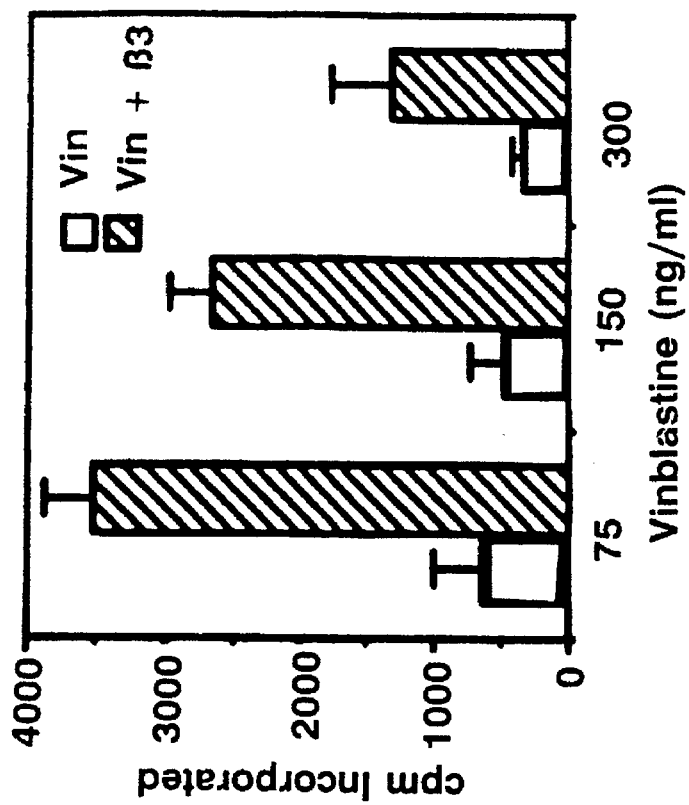
FIGS. 1A and 1B: Evaluation of TGF-β3 as a chemoprotective agent of epithelial cells in vitro, challenging mink cells with colchicine(1a) and vinblastine(1b).

As used herein, TGF-β means a protein which exists in vivo as a covalently linked dimer having a molecular weight ≈25,000. The term TGF-β means and includes natural and recombinant TGF-β1 (TIF), TGF-β2, TGF-β3 (TGI, TGI-1, TGI-2), TGF-β4, TGF-β5, or TGF-β heterodimers including TGF-β1.2 and TGF-β2.3. The natural TGF-β may be purified from tissue such as bone, platelets, or placenta or, more preferably prepared using recombinant technology (Iwata, et al. 1992 A; ten Dijke et al. 1990 A; ten Dijke et al. 1990 B; Purchio et al., 1990; Derynck et al., 1988; Jakolaw et al., 1988; Cerletti, N., 1991; Ogawa et al., 1992).

As used herein, Transforming Growth Factor Beta means and includes 1) TGF-β; 2) a biologically active homolog of TGF-β; 3) biologically active mutants of TGF-β; and 4) biologically active variants of TGF-β. In this respect biologically active means having substantially the same biological activity as native TGF-β, e.g. binding to Type I or Type II TGF-β receptors and inhibiting Mink Lung cell line CCL64. Mutants and variants may be polypeptides in which the amino acid sequence has been changed but are still biologically active including deletion mutants, substitution mutants, variants with amino acid substitutions. In addition, Transforming Growth Factor Beta means and includes variants capable of binding to the Type I or Type II receptors in which the biological activity has been mediated.

This invention provides a method of preventing oral mucositis in a subject susceptible to mucositis which comprises administering to the subject a prophylactically effective amount of a Transforming Growth Factor Beta. Preferably, such administration is effected prior to antineoplastic therapy, such as chemotherapy or radiation treatment for the subject. The administration may continue through a cycle of chemotherapy, for up to five days in order to retain its protective effect. The methods described herein are particularly suited for treating pediatric subjects.

Transforming Growth Factor Beta is useful in preventing epithelial cell damage during chemotherapy. Transforming Growth Factor Beta inhibits the proliferation of a variety of normal epithelial cell types and hematopoietic stem cells, in contrast to tumor cells which often are impaired in their ability to transduce signals mediated by TGF-β3 binding to type I or type II TGF-β receptors. Thus, tumor cells are generally less responsive to the growth inhibiting effects of TGF-β3. The ability of TGF-β3 to reversibly inhibit cycling of normal hematopoietic stem cell or epithelial cell types, but not many tumor cell types, allow TGF-β to be used to as a chemoprotectant of normal tissue during cytotoxic chemotherapy. TGF-β3-mediated protection of the oral mucosa is valuable in reducing severe and painful mucositis. Implementation of this therapeutic approach represent a major advance in cancer management.

Preferably, the administration is topical. Dose ranges for topical use include 1 ng to 10 mg per dose, more preferably, 10 ng to 100 µg per dose or even more preferably 50 ng to 20 µg per dose. However, the administration may also be systemic. Dose ranges for systemic application include 1 ng to 500 µg/kg subject weight/day, preferably 80 ng to 100 µg/kg subject weight/day, or more preferably 1 µg to 20 µg/kg subject weight/day.

Chemotherapy agents which cause oral mucositis include, but are not limited to 5-FU, doxorubicin (Adriamycin) daunorubicin, methotrexate, vincristine, vinblastine, Melphalan, cytosine arabinoside, thioguanine, bleomycin, dactinomycin, cisplatin, mithramycin, mitomycin, hydroxyurea and procarbazine hydrochloride. Patients receiving high dose or accelerated cycle chemotherapy are at risk of developing oral mucositis, as are pediatric patients, patients undergoing bone marrow transplantation and patients receiving radiation therapy for squamous carcinoma of the head and neck.

A "prophylactically effective amount" as used herein refers to that amount which provides a prophylactic effect by preventing oral mucositis in a subject receiving a given condition and administration regimen. Compositions comprising prophylactically effective amounts together with suitable diluents, preservatives, solubilizers, emulsifiers, adjuvants and/or carriers useful for Transforming Growth Factor Beta therapy. Such compositions are liquids or lyophilized or otherwise dried formulations and include diluents of various buffer content (e.g., Tris-HCL, acetate phosphate), pH and ionic strength, additives such as albumin or gelatin to prevent absorption to surfaces, detergents (e.g., Tween 20, Tween 80, Pluronic F68, bile acid salts), solubilizing agents (e.g., Thimerosal, benzyl alcohol), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, polyvinyl pyrrolidone, etc. or into liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance of Transforming Growth Factor Beta. Other ingredients optionally may be added such as antioxidants, e.g., ascorbic acid; low molecular weight (less than about ten residues) polypeptides, i.e., polyarginine or tripeptides; proteins, such as serum albumin, gelatin, or immunoglobulins; amino acids; such as glycine, glutamine acid, aspartic acid, or arginine; chelating agents such as EDTA; and sugar alcohols such as mannitol or sorbitol. The choice of composition will depend on the physical and chemical properties of the Transforming Growth Factor Beta. Controlled or sustained release compositions include formulation of lipophilic depots (e.g., fatty acids, waxes, oils). Also comprehended by the invention are particulate compositions coated with polymers (e.g., poloxamers or poloxamines) and Transforming Growth Factor Beta coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral.

Suitable topical formulations include gels, creams, solutions, emulsions, carbohydrate polymers, biodegradable matrices thereof; vapors, mists, a aerosols, or other inhalants. Transforming Growth Factor Beta may be encapsulated in a wafer, wax, film or solid carrier, including chewing gums. Permeation enhancers to aid in transport to movement across the epithelial layer are also known in the art and include, but are not limited to, dimethyl sulfoxide and glycols. Suitable vehicles are described above. The Transforming Growth Factor Beta so administered may be immobilized so as to prevent dilution and washing by saliva. Such agents are also known in the art and include but are not limited to methyl-propylcellulose.

This invention is illustrated in the Experimental Detail section which follow. These sections are set forth to aid in an understanding of the invention but are not intended to, and should not be construed to, limit in any way the invention as set forth in the claims which follow thereafter.

EXPERIMENTAL DETAILS

EXAMPLE 1

EVALUATION OF TGF-β ACTIVITY IN VITRO ON SEVERAL HUMAN CELL LINES TYPES

Cell growth was determined using the monolayer assay for TGF-β3 described by Iwata (Iwata, et al. 1992 B). Non-leukemic cells were subcultured on 96-well tissue culture plates in 100µl of media at a seeding density of $2 \times 10^3$ cells per well. Cells were maintained and assayed in Dulbecco's modified Eagle's medium containing 10% fetal bovine and 2% L-glutamine. These cells were treated with 25 ng/ml (1 nM) of TGF-β3, pulsed 24 hours with 1 µCi/ml 5-[$^{125}$I]-iodo-2'deoxyuridine when cells in the untreated control wells were 90% confluent and harvested.

Table 1 shows inhibition of some human tumor lines by TGF-β3.

TABLE 1

Effects of TGF-β3 (1 nM) on the Growth of Human Epithelial Derived Cancer Cell Lines in Culture

| CELL LINE | | % INHIBITION |
|---|---|---|
| Human Epithelial Derived Cancer Lines | | |
| A549 | (lung adenocarcinoma) | 46 |
| A375 | (melanoma) | 47 |
| A2058 | (melanoma) | 88 |
| WiDR | (colon adenocarcinoma) | 24 |
| MCF 7 | (breast carcinoma) | 57 |
| Normal Human | | |
| Hff | (foreskin fibroblasts) | 6 |

EXAMPLE 2

In vitro protection of epithelial cells against chemotherapeutic drugs
Mink Epithelial cells In order to evaluate Transforming Growth Factor Beta as a protective agent in vitro the following experiment was performed.

Mink cells were seeded in 96-well plates at $10^3$ cells/well in 100 µl of DMEM supplemented with 10% fetal bovine serum. Wells containing treated cells received 25 µl of TGF-β3 (50 ng/ml). After 24 hours incubation with TGF-β3, 25 µl of colchicine or vinblastine was added. After another 24 hours, the media was removed and the cells washed once with Dulbecco's PBS and fresh complete media added. The cells were incubated for another 7 days.

Figure 1B:
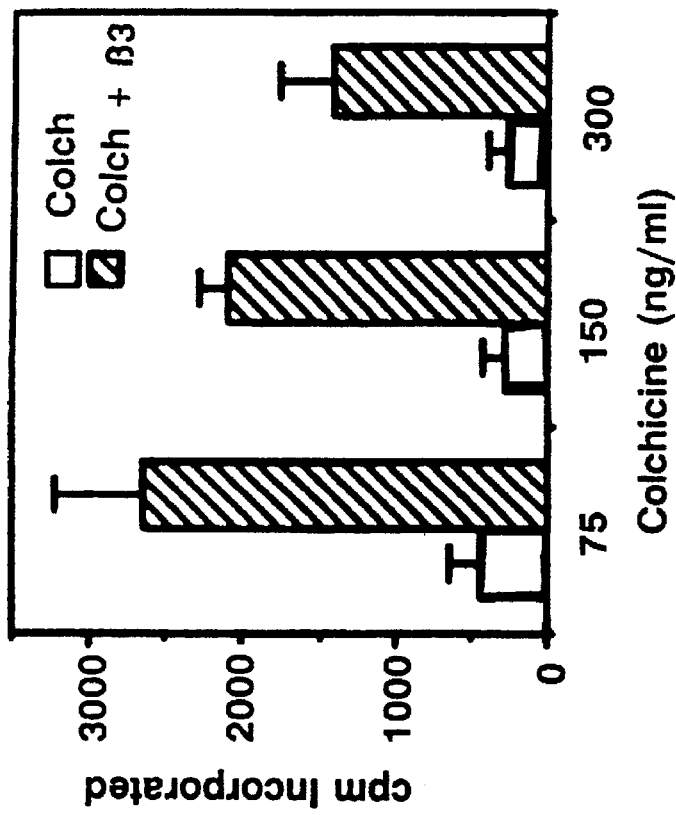
Figure 2C:
FIG. 2: Hamster cheek pouches on (A) day 9; (B) day 11; and (C) day 13 post primary treatment with 5-FU, with placebo treatment (Group 1), 2 µg TGFβ3 topical treatment (Group 2), or 20 µg TGFβ3 topical treatment (Group 3).
Figure 3:
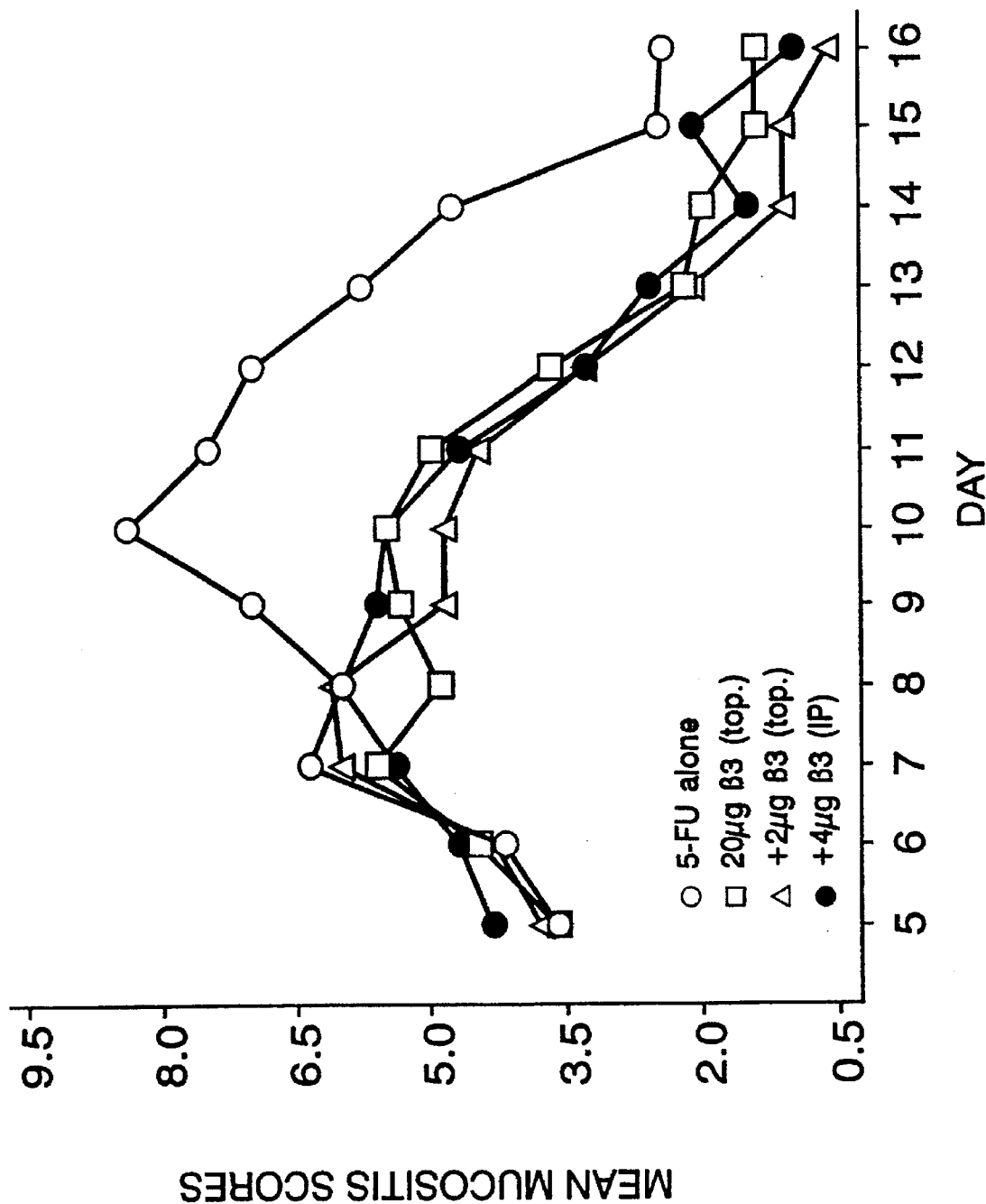
FIG. 3: Mean mucositis scores on days 5 through 16 of hamsters treated i.p. with 5-FU on days 0 and 2 at doses of 60 mg/kg and 40 mg/kg respectively. Group 1: (Open circles) treatment with 5-FU alone. Group 2: (Open triangles) treatment with 5-FU and 2 µg TGFβ3 topically. Group 3: (Open squares) treatment with 5-FU and 20 µg TGFβ3 topically. Group 6 (Filled circles) treatment with 5-FU and 4 µg TGFβ3 intraperitoneally.
Figure 4:
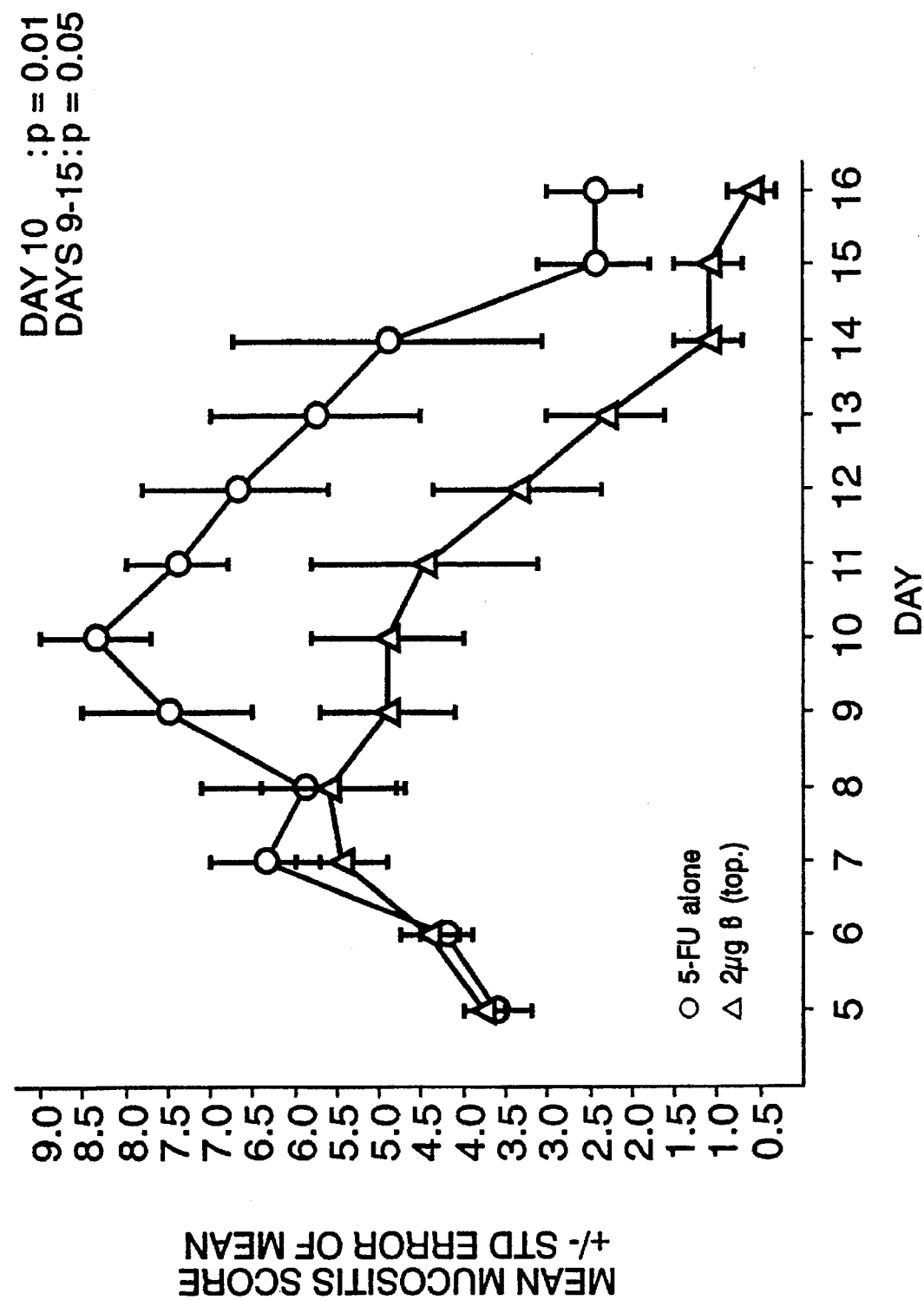
FIG. 4: Statistical significance data for Group 1: (Open circles) treated with 5-FU alone. Group 2: (Open triangles) 5-FU with 2 µg TGFβ3 topically. Error bars represent the standard error about the mean mucositis score.
Figure 5:
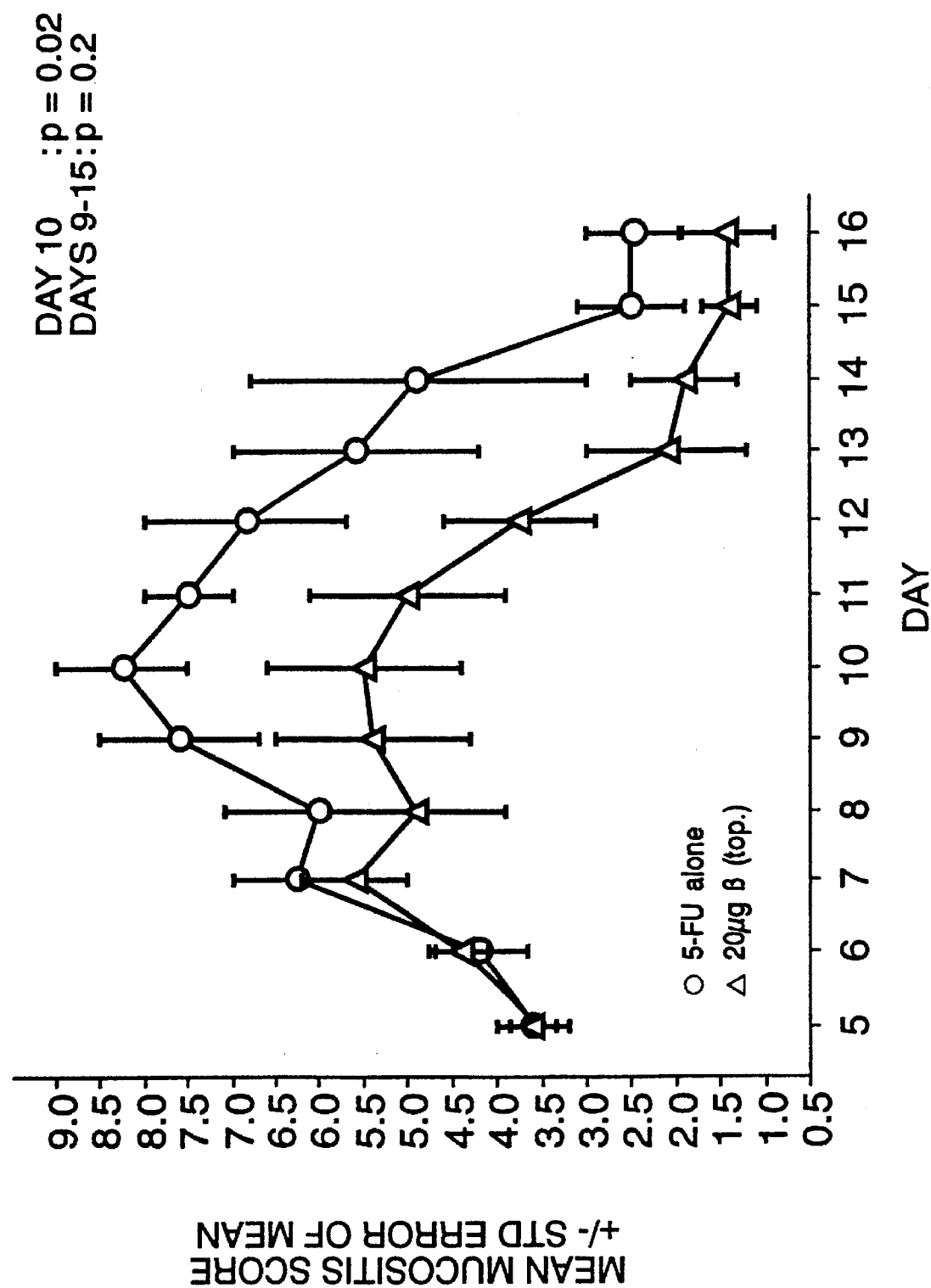
FIG. 5: Statistical significance data for Group 1: (open circles) treated with 5-FU alone. Group 3: (open triangles) 5-FU with 20 µg TGFβ3 topically. Error bars represent the standard error about the mean mucositis score.

Cell growth was quantitated by uptake of 5-[$^{125}$I]iodo-2'deoxyuridine ($^{125}$IUdR) indicating the amount of cell growth as described (Iwata et al., 1992 B). As seen in FIGS. 1A and 1B, cells preincubated with TGF-β3 prior to incubation with various doses of chemotherapeutic drugs (i.e. vinblastine and colchicine) showed significantly more uptake of $^{125}$IUdR relative to cells which were incubated with the chemotherapeutic drugs without TGF-β3. Therefore, cells preincubated with TGF-β3 were protected from the toxic effects of the chemotherapeutic drugs. Similar results were observed when adriamycin was used as the chemotherapeutics drug. This protective effect should also be possible with other chemotherapeutic drugs.

For Transforming Growth Factor Beta to be effective in protecting normal epithelial cells from chemotherapy it is apparent that the growth of the tumor is preferably less inhibited than that of normal tissues. This may be achieved either because the tumor is innately resistant to the growth inhibitory effects of Transforming Growth Factor Beta or via the pharmacokinetics allowing a differential effect in vivo.

EXAMPLE 3

In vivo inhibition of oral epithelial proliferation by topical application of Transforming Growth Factor Beta Transforming Growth Factor Beta prevents oral mucositis by inhibiting the proliferation of the oral epithelium, rendering this tissue less sensitive to the cytotoxic effects of chemotherapy. We show topical administration of Transforming Growth Factor Beta to the buccal cavity of hamsters acts to decrease the fraction of oral epithelial cells in S-phase, and thereby inhibit cell proliferation. In this example the buccal pouch of Golden Syrian hamsters were treated with 0 µg, 2 µg, 20 µg or 200 µg of TGF-β3 in a saline diluent and subsequently covered with methyl-propylcellulose.

Three topical TGF-β3 applications were made over an eight hour time period. Only the left cheek was treated; the right cheek served as a control. Biopsies of the cheek pouch were obtained approximately 16 hours after the final TGF-β3 treatment. The biopsied oral tissue was formalin fixed, embedded in paraffin, sectioned and immunohistologically stained with a monoclonal antibody to PCNA (a marker of S-phase cells). Alternatively, Ki67 antibody staining of sectioned tissue or $^3$H-thymidine labelling of the oral epithelium in vivo may be used to measure cell division in vivo. Sixteen hours post TGF-β3 treatment the following data was obtained (Table 2):

Table 2

In vivo Inhibition of Oral Epithelial Proliferation shown by PCNA Staining of Hamster Oral Mucosa after Topical Administration of TGF-β3.

| Topical Treatment | Mean Inhibition vs. Control |
|---|---|
| 2 µg TGF-β3 | 22% |
| 20 µg TGF-β3 | 42% |
| 200 µg TGF-β3 | 46% |

This data show Transforming Growth Factor Beta to be a potent inhibitor of the cell cycling of oral epithelium in vivo.

EXAMPLE 4

Transforming Growth Factor Beta as an Agent Useful for the Prevention of Mucositis The rationale for administration of Transforming Growth Factor Beta in cancer therapy is to inhibit or slow cycling of the oral mucosa cells prior to chemotherapy or radiation therapy, thus decreasing the side effects of conventional chemotherapy and allowing the implementation of significantly more aggressive chemotherapeutic regimens.

An animal model is used to evaluate in vivo efficacy of Transforming Growth Factor Beta as an agent useful for prevention of oral mucositis in hamsters induced by the chemotherapeutic agent 5-FU (Sonis et al., 1990). A number of 5-FU schedules may be useful to produce mucositis and assess therapeutic standards. In one protocol, groups of 12, eight week old Golden Syrian hamsters are given 5-FU (60 mg/kg) on days 0, 5 and 10. Alternatively, 5-FU may to administered on days 0 and on day 2 by the intraperitoneal (i.p.) route in doses of 60 mg/kg and 40 mg/kg, respectively. Animals are observed and weighed daily. The animals are anesthetized with ether and the buccal cavity everted and photographed. Photographs of the cheek pouch are numbered, randomized, independently scored blind by four clinicians using a common set of grading photographs. This approach, grading oral mucositis on scale from 1 to 10, results in statistically significant data. As in man, oral mucositis peaks around 7 days from initial exposure to 5-FU. Importantly, oral mucositis is worse when the epithelium is actively dividing (e.g. TGF-α pretreated), mimicking the situation with pediatric chemotherapy patients.

Biological activity in vivo is shown by administering TGF-β to the oral epithelium of hamsters in a suitable carrier in order to demonstrate the dose and schedule relationship to effect a lengthening or arrest of the normal epithelial cell cycle. Prevention of oral mucositis is shown by pretreatment of hamsters with Transforming Growth Factor Beta prior to 5-FU treatment. Mucositis is graded on a scale of 1 to 10 as described above. Schedule and dose relationship to efficacy is demonstrated using the same animal protocol.

In this example TGF-β3 was administered to the hamster oral cavity to prevent mucositis. The following groups of 10 Golden Syrian hamsters (age ≈6 weeks) were evaluated for the severity and duration of mucositis following 5-FU treatment using the days 0 and 2 schedule described above. The following groups were evaluated:

TABLE 3

| Group (N = 10) | TGF-β3 | Schedule of TGF-β3 admin | Route |
|---|---|---|---|
| 1 | 4 × vehicle alone | over 24 hrs. day -1 to day 0 | topical |
| 2 | 4 × 2 µg | over 24 hrs. day -1 to day 0 | topical |
| 3 | 4 × 20 µg | over 24 hrs. day -1 to day 0 | topical |
| 6 | 3 × 4 µg | over 8 hrs. day -2 | intraperitoneal |

Figure 6:
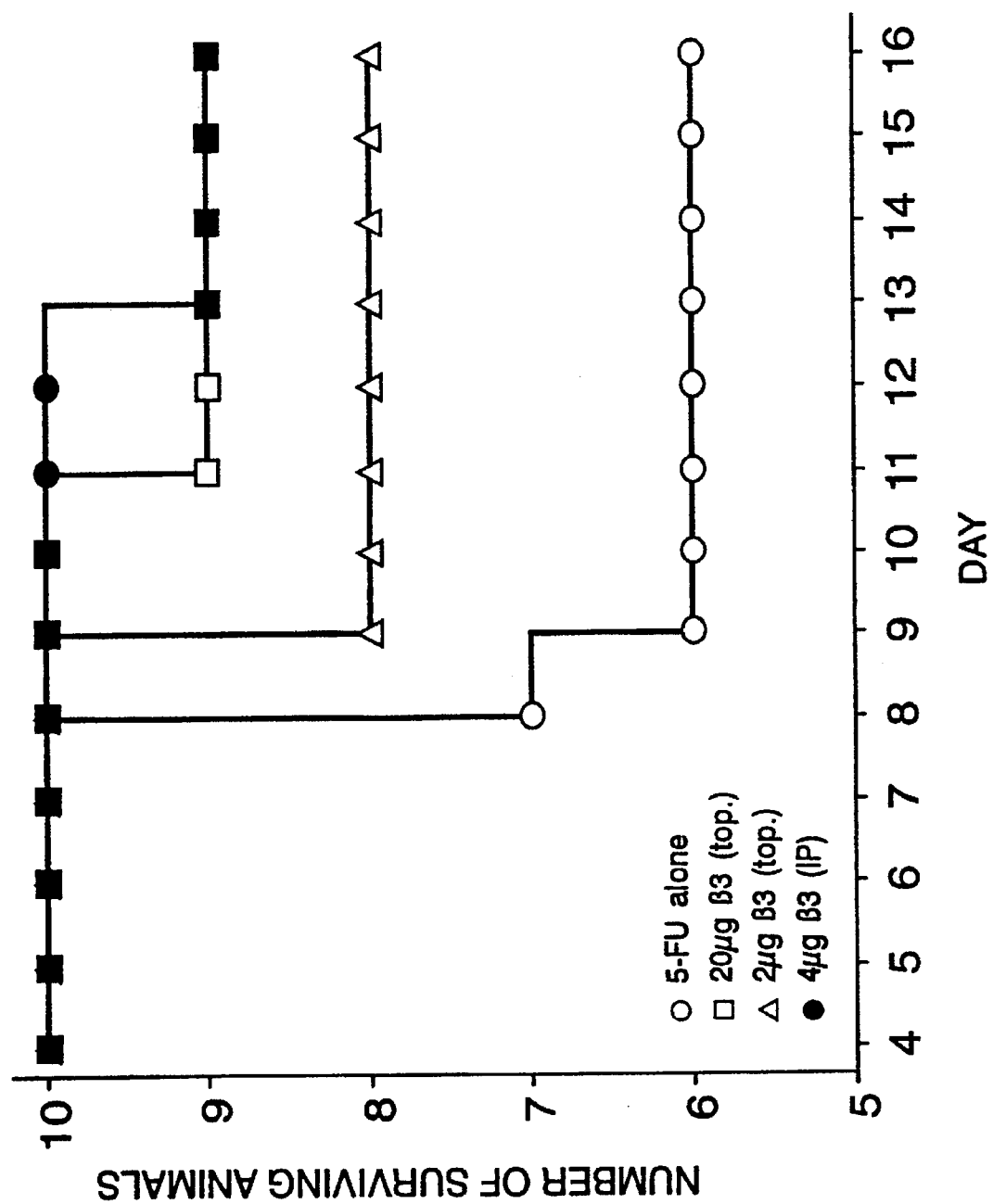
FIG. 6: Survival data days 4–16 for Group 1: (open circles) treated with 5-FU alone. Group 2: (open triangles) 5-FU+2 µg TGFβ3 topically. Group 3: (open squares) 5-FU and 20 µg TGFβ3 topically. Group 6: (solid circles) 5-FU and 4 µg TGFβ3 intraperitoneally.
Figure 7:
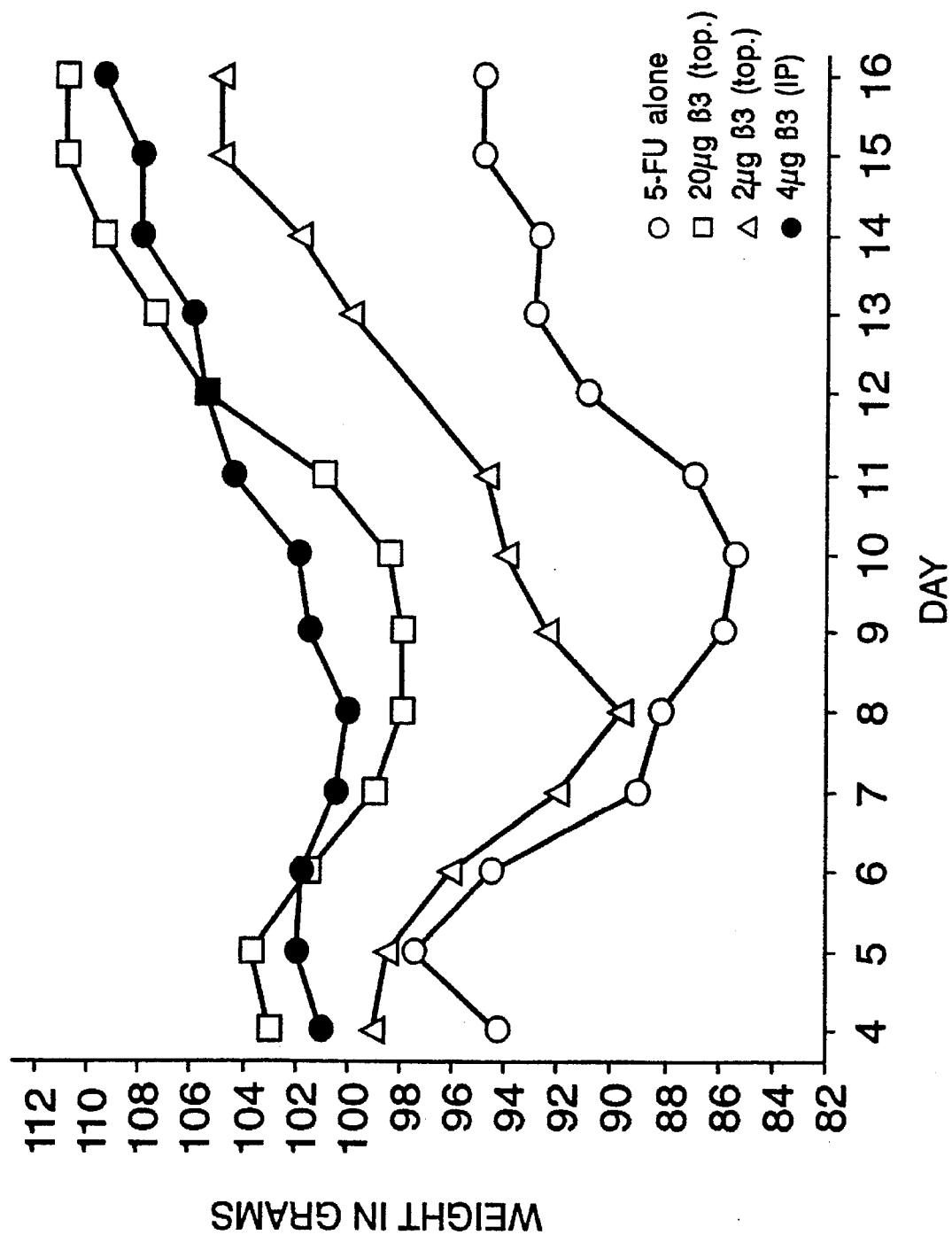
FIG. 7: Average weight curves for days 4–16. Group 1: (open circles) treated with 5-FU alone. Group 2: (open triangles) 5-FU and 2 µg TGFβ3 topically. Group 3: (open squares) 5-FU and 20 µg TGFβ3 topically. Group 6: (filled circles) 5-FU and 4 µg TGFβ3 intraperitoneally.

These data were statistically significant and conclusively show TGF-β3 reduces the severity and duration of mucositis in vivo (FIGS. 2–5). Increased survival (FIG. 6) and weight retention (FIG. 7) were also observed. This effect was achieved through cell cycle inhibition of the oral epithelium prior to chemotherapy, and not apparently by accelerated wound healing, as shown by Example 5.

Topical administration (i.e. direct application) of Transforming Growth Factor Beta to the oral mucosa is the preferred route of administration, though systemic administration by i.v. bolus or continuous infusion are also suitable. Compositions suitable for application of Transforming Growth Factor Beta to the buccal cavity are known in the art and have been described above.

The effective amount of Transforming Growth Factor Beta in the carrier vehicle ranges from 0.01 µg to 10 mg depending on the extent or severity of the oral mucositis. Transforming Growth Factor Beta is applied to the buccal cavity in a suitable physiological carrier up to 5 days prior to treatment with one or more cytotoxic chemotherapy agents.

Clinical Evaluation and Patient Administration

Based on scheduling data and dosage data derived by modelling in the Golden Syrian hamster, Phase I trials are conducted to evaluate safety. Little or no toxicity is anticipated in acute topical administration of Transforming Growth Factor Beta to the oral cavity. Dose escalation studies and chronic exposure studies may be performed. In Phase II patients are evaluated for a reduction in the frequency and severity of oral mucositis associated with chemotherapy. In clinical practice, patients are protected from oral mucositis by topical or systemic administration of Transforming Growth Factor Beta in a suitable carrier prior to chemotherapy. Administration of Transforming Growth Factor Beta may be continued for a period after chemotherapy i.e. that period of pharmacologic exposure to ensure protection of the oral tissue from the chemotherapeutic agent. The dose range of Transforming Growth Factor Beta administered to patients is determined first by modelling in the hamster and is refined in Phase I/Phase II trials. The amount of Transforming Growth Factor Beta applied to the oral cavity in these range finding studies is determined empirically. The patient is monitored for oral mucositis according to several well established scoring criteria, for example the ECOG score for oral mucositis. The dose or schedule of Transforming Growth Factor Beta administered to the cancer patient may be adjusted in subsequent rounds of chemotherapy, according to the extent or duration of oral mucositis in the first round of therapy.

EXAMPLE 5

Addition treatment with Transforming Growth Factor Beta after 5-FU treatment

To evaluate the effects of Transforming Growth Factor Beta post second 5-FU treatment, two additional groups were treated in the same way as Groups 2 and 3, but also receiving topical, oral Transforming Growth Factor Beta following the second dose of 5-FU as shown in Table 4.

TABLE 4

| Group | TGF-β3 post 5-FU | Time of TGF-β3 | Route |
|---|---|---|---|
| 4 | 6 × 2 µg | twice daily days 5, 6 and 7 | topical |
| 5 | 6 × 20 µg | days 5, 6 and 7 | topical |

Figure 8:
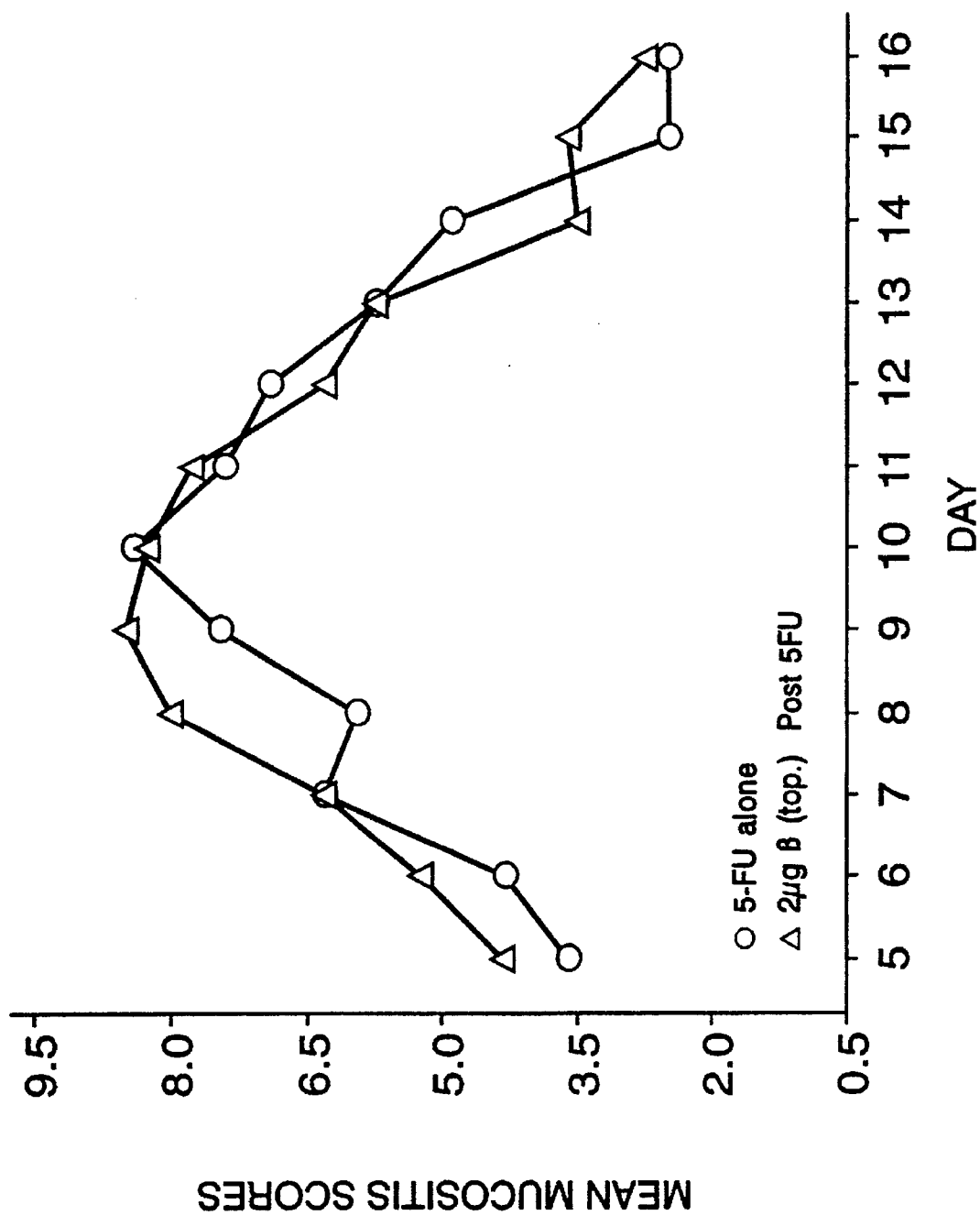
FIG. 8: Mean mucositis scores for Group 1: (open circle) 5-FU alone. Group 4: (open triangles) 5-FU and additional 2 µg TGFβ3 topically administered post-5-FU, twice daily on days 5, 6 and 7.

Transforming Growth Factor Beta post 5-FU administration was not effective in preventing mucositis as shown in FIGS. 8 and 9. No significant differences in mucositis scores were observed between groups 1, 4 and 5. Thus, unlike TGF-α, EGF, or PDGF, administration of topical Transforming Growth Factor Beta after chemotherapy has no therapeutic beneficial effect, unlike TGF-β pretreatment, and therefore is contraindicated. In this setting and dose TGF-β is a negative regulator of epithelial cell growth, not an oral tissue positive growth factor like TGF-α, EGF, and PDGF.

REFERENCES

Cerletti, N. et al., European Patent Publication No. 0 433, 225 A1, published Jun. 19, 1991.

Derynck R., et al., U.S. Pat. No. 4,886,747, issued Dec. 12, 1990.

Gesme "Preventing Mucositis with Cryotherapy" Contemporary Oncology (1992) 2:35.

Graycar, J. L., et al., (1989) *Molecular Endocrinology;* 3(12):1977–1986

Guggenheimer, J., Verbin, R. S., Appel, B. N., Schmitz, J. "Clinicopathologic effects of cancer chemotherapeutic agents on human buccal mucosa." Oral Surg. Med. Oral Pathol., (1977) 44:58–63.

Iwata, K. K., et al., (1992 A) International Publication No. WO 92/00318, published Jan. 9, 1992.

Iwata, K. K., et al., (1992 B) International Publication No. WO 92/00330, published Jan. 9, 1992.

Jakowlaw et al. (1988) Mol. Endocrinology 2:1186–1196.

Lockhart, O. B., Sonis, S. T., "Alterations in the oral mucosa cause by chemotherapeutic agents," J. Dermatol Surg (1981) 7:1019–25.

Massague J., Cell, 49:457–458 (1987).

Purchio, A. F., et al., UK Patent Publication No. GB-2210620A, published Jun. 14, 1990.

Ogawa, Y. et al., (1992) J. Biol. Chem. 267:2325.

Sonis, S., et al., "Oral Complications in Patients Receiving Treatment for Malignancies Other Than of the Head and Neck" JADA, Sep. 1978, 97:468–472.

Sonis, A., and Sonis, S., "Oral Complications of Cancer Chemotherapy in Pediatric Patients" Journal of Pedodontics, (Winter 1979) 122–128.

Sonis, S., et al., "Impact of Improved Dental Services on the Frequency of Oral Complications of Cancer Therapy for Patients With Non-Head and Neck Malignancies" Oral Surg, January 1988, 65:19–22.

Sonis, S., et al., "An Animal Model For Mucositis Induced by Cancer Chemotherapy" Oral Surg. Oral Med. Oral Pathol. April 1990, 69:437–443.

Sonis, S., "Oral Complications of Cancer Therapy" In: *Cancer Principles and Practice or Oncology.* Volume 2, 3rd Edition. J. B. Lippincott Company, Philadelphia 1990.

Sonis, S., and Clark, J., "Prevention and Management of Oral Mucositis Induced By Antineoplastic Therapy" *Oncology,* December 1991, Vol. 5(12):11–17.

ten Dijke, P. et al, (1990 A) International Publication No. WO 90/14360, published Nov. 29, 1990.

ten Dijke, P., et al., (1990 B) Molecular Characterizations of Transforming Growth Factor Type, Annals of New York Academy, pp. 26–42

What is claimed is:

1. A method of preventing chemotherapy or radiation therapy induced oral mucositis in a subject which comprises administering to the subject a composition consisting essentially of a prophylactically effective amount of TGF-$\beta$3, said administration to the subject being commenced at least 24 hours prior and not more than five days prior to a given cycle of chemotherapy or radiation therapy and not continuing for more than five days during such cycle nor continuing after cessation of such cycle of chemotherapy or radiation therapy.

2. A method of claim 1, wherein the TGF-$\beta$3 is a recombinant TGF-$\beta$3.

3. A method of claim 1, wherein the subject is a pediatric subject.

4. A method of claim 1, wherein the administration is topical.

5. A method of claim 3, wherein the topically administered amount is between 1 ng and 10 mg.

6. A method of claim 1, wherein the administration is systemic.

7. A method of claim 6, wherein the systemically administered amount is between 1 ng and 500 µg/kg weight/day.

8. The method of claim 1, wherein the oral mucositis is chemotherapy induced oral mucositis.

9. The method of claim 1, wherein the oral mucositis is radiation therapy induced oral mucositis.

* * * * *